US00H002158H

(19) United States
(12) Statutory Invention Registration
Krenmüller et al.

(10) Reg. No.: US H2158 H
(43) Published: Jun. 6, 2006

(54) PROCESS FOR THE PRODUCTION OF CLAVULANIC ACID SALTS

(75) Inventors: Franz Krenmüller, Kufstein (AT); Harald Summer, Woergl (AT)

(73) Assignee: Sandoz AG, Basel (CH)

(21) Appl. No.: 10/437,097

(22) Filed: May 13, 2003

(65) Prior Publication Data

US 2003/0203886 A1 Oct. 30, 2003

Related U.S. Application Data

(63) Continuation of application No. 10/251,948, filed on Sep. 20, 2002, now abandoned, which is a continuation of application No. 10/071,364, filed on Feb. 8, 2002, now abandoned, which is a continuation of application No. 09/892,179, filed on Jun. 26, 2001, now abandoned, which is a continuation of application No. 09/588,390, filed on Jun. 6, 2000, now abandoned, which is a continuation of application No. 09/401,427, filed on Sep. 22, 1999, now abandoned, which is a continuation of application No. 09/236,013, filed on Jan. 22, 1999, now abandoned, which is a continuation of application No. 08/837,536, filed on Apr. 21, 1997, now abandoned, which is a continuation of application No. 08/263,868, filed on Jun. 21, 1994, now abandoned, which is a continuation of application No. 08/028,486, filed on Mar. 9, 1993, now abandoned.

(30) Foreign Application Priority Data

Mar. 10, 1992 (AT) ..... A472/92

(51) Int. Cl.
*C07D 503/18* (2006.01)

(52) U.S. Cl. ..... 540/349

(58) Field of Classification Search ..... None
See application file for complete search history.

(56) References Cited

U.S. PATENT DOCUMENTS

| | | | | |
|---|---|---|---|---|
| 3,288,800 | A | 11/1966 | Heuser et al. | 260/306.7 |
| 4,110,165 | A | 8/1978 | Cole et al. | 195/80 |
| 4,144,242 | A | 3/1979 | Fleming | 540/349 |
| 4,454,069 | A | 6/1984 | Cook et al. | 540/349 |
| 4,556,559 | A | 12/1985 | Cole et al. | 424/114 |
| 4,560,552 | A | 12/1985 | Cole et al. | 424/114 |
| 4,647,659 | A | 3/1987 | Cook et al. | 540/349 |
| 4,795,824 | A | 1/1989 | Kippax | 560/204 |
| 5,210,296 | A | 5/1993 | Cockrem | 562/589 |
| 5,310,898 | A | 5/1994 | Copar | 540/349 |
| 5,614,199 | A | 3/1997 | Zmitek et al. | 424/400 |
| 5,679,789 | A | 10/1997 | Clark et al. | 540/349 |
| 5,726,170 | A | 3/1998 | Callewaert | |
| 5,734,048 | A | 3/1998 | Kim | |

FOREIGN PATENT DOCUMENTS

| | | |
|---|---|---|
| EP | 02312 | 6/1979 |
| EP | 26044 | 4/1981 |
| EP | 277008 | 1/1988 |
| EP | 312813 | 4/1989 |
| EP | 387178 | 9/1990 |
| EP | 594099 | 4/1994 |
| EP | 672669 | 9/1995 |
| GB | 1508977 | 4/1978 |
| GB | 2003863 | 3/1979 |
| GB | 1543563 | 4/1979 |
| GB | 1561395 | 2/1980 |
| GB | 1578739 | 11/1980 |
| GB | 2287025 | 9/1995 |
| GB | 2298201 | 8/1996 |
| PL | 139811 | 4/1988 |
| WO | WO 93/25557 | 12/1993 |
| WO | WO 95/21173 | 8/1995 |
| WO | WO 95/23870 | 9/1995 |
| WO | WO 95/34194 | 9/1995 |
| WO | WO 96/33197 | 4/1996 |
| WO | WO 96/28452 | 9/1996 |
| WO | WO 97/05142 | 2/1997 |
| WO | WO 97/08175 | 3/1997 |
| WO | WO 97/47301 | 12/1997 |
| WO | WO 98/21212 | 5/1998 |

OTHER PUBLICATIONS

Chem. Abstr. vol. 87–6692, 1996.
Abstract of JP 55162993 (CA vol. 94:137803), 1996.
Chem. Abstr. vol. 99–37107, 1996.
Communication Pursuant to Article 115(2) EPC from file of EP 672,669 dated Apr. 3, 1997, the response dated May 30, 1997, and Minutes of Oral Proceedings dated Jun. 27, 1997.
International Search Report.

*Primary Examiner*—Mark L. Berch
(74) *Attorney, Agent, or Firm*—John D. Thallemer

(57) ABSTRACT

Use of the 2-amino-2,4,4-trimethylpentane salt of clavulanic acid as an intermediate in the production of pharmaceutically acceptable salts of clavulanic acid.

22 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PROCESS FOR THE PRODUCTION OF CLAVULANIC ACID SALTS

This application is a continuation of application Ser. No. 10/251,948, filed Sep. 20, 2002 abandoned; which is a continuation of application Ser. No. 10/071,364, filed Feb. 8, 2002, abandoned; which is a continuation of application Ser. No. 09/892,179, filed Jun. 26, 2001, abandoned; which is a continuation of application Ser. No. 09/588,390, filed Jun. 6, 2000, abandoned; which is a continuation of application Ser. No. 09/401,427, filed Sep. 22, 1999, abandoned; which is a continuation of application Ser. No. 09/236,013, filed Jan. 22, 1999, abandoned; which is a continuation of application Ser. No. 08/837,536, filed Apr. 21, 1997, abandoned; which is a continuation of application Ser. No. 08/263,868, filed Jun. 21, 1994, abandoned; which is a continuation of application Ser. No. 08/028,486, filed Mar. 9, 1993, abandoned.

The invention relates to a new process for the production of pharmaceutically acceptable salts of clavulanic acid.

Clavulanic acid is of special interest as an additive to β-lactam antibiotic formulations because of its inhibiting activity on β-lactamases. β-lactamases are enzymes which open the β-lactam ring of penicillins and cephalosporins, whereupon their anti-bacterial effectiveness is lost. β-lactamases are formed by many bacteria and they are the cause of the resistance thereof towards penicillins and cephalosporins (resistance formation). It has therefore proved advantageous to use β-lactam antibiotics in a mixture with clavulanic acid or its pharmaceutically acceptable salts, whereby the effectiveness of the β-lactam is fully maintained even in the presence of β-lactamase-producing bacteria. One example of this is the commercially-available combination of amoxicillin and clavulanic acid potassium salt, which is broadly used in the control of infectious diseases.

Clavulanic acid is obtained by fermentation of Streptomyces clavuligerus, and isolated and purified by complicated processes, e.g. those described in DOS 2 517 316. After separating the cell mass, the filtrate is acidified, and the clavulanic acid is extracted with an organic solvent, e.g. n-butanol. After renewed re-extraction into an aqueous solution, technologically complicated and economically expensive purification processes follow, such as chromatography by means of ion exchange resins or gel chromatography. EP-B-00 26 044 describes the use of the tert.butylamine salt of clavulanic acid as an intermediate product in the isolation thereof. The salt is hereby crystallized out of acetone-containing organic solvent mixtures as an acetone solvate. When the tert.butylamine salt of clavulanic acid is converted into pharmaceutically acceptable salts of clavulanic acid, acetone is distributed into the reaction mixture, thus complicating the process of working up and recycling of the solvents.

In EP-A-0 387 178 the use of organic amine salts for the isolation of clavulanic acid is described. The amine may be primary, secondary or tertiary and may be substituted by aliphatic hydrocarbon radicals having up to 7 C-atoms or by aromatic radicals. Examples of different crystalline amine salts of clavulanic acid are disclosed. However our attempts to reproduce these amine salts in crystalline form failed except for the bases sec.-butylamine and benzyl tert.butylamine. While the former produces the amine salt of clavulanic acid only slowly and with poor crystallisation tendency, thus affecting the purity of the salt, the second amine is uncommon and very expensive.

For pharmaceutical application of the active material, the above-mentioned amine salts of clavulanic acid are preferably converted into their pharmaceutically acceptable alkali salts, especially the potassium salt. This is effected by dissolving the amine salt in a solvent optionally with addition of water and adding to it a solution of a readily soluble alkali salt, e.g. sodium or potassium-2-ethylhexanoate, whereby the poorly soluble alkali salt of clavulanic acid crystallises out and may be isolated. Due to the poor solubility of the said amine salts in suitable organic solvents, it is necessary to add water, whereupon the solubility is improved. However, this necessary addition undesirably also raises the solubility of the alkali salt of clavulanic acid which is precipitated later, and thus causes a loss in yield.

There was still a strong demand in the art for an improved process of preparing pharmaceutically acceptable salts of clavulanic acid. It has surprisingly been found that the object can be attained by the use of a specific amine salt of clavulanic acid.

Accordingly to the present invention, there is provided a process for the production of a pharmaceutically acceptable salt of clavulanic acid, which comprises forming the 2-amino-2,4,4-trimethylpentane salt of clavulanic acid and converting this salt into a pharmeceutically acceptable salt of clavulanic acid.

Clavulanic acid may be isolated as the 2-amino-2,4,4-trimethylpentane salt most advantageously in high yield and highly pure form from an organic solution of impure clavulanic acid, obtained for instance by extraction with an organic solvent from fermentation broth or the filtrate thereof. The 2-amino-2,4,4-trimethylpentane salt of clavulanic acid has been disclosed in U.S. Pat. No. 4,650,795, but only with regard to its use in pharmaceutical formulations and not for the isolation and purification of clavulanic acid.

In particular the present invention provides a process for the preparation of pharmaceutically acceptable salts of clavulanic acid comprising a) treating a solution of clavulanic acid in a organic solvent, as is optionally obtained by extraction from a fermentation broth or from a filtrate derived therefrom, with 2-amino-2,4,4-trimethylpentane, b) isolating the 2-amino-2,4,4-trimethylpentane salt of clavulanic acid and optionally recrystallising the 2-amino-2,4,4-trimethylpentane salt of clavulanic acid and c) converting the obtained 2-amino-2,4,4-trimethylpentane salt of clavulanic acid into a pharmaceutically acceptable salt of clavulanic acid.

In another aspect the present invention provides the use of the 2-amino-2,4,4-trimethylpentane salt of clavulanic acid as an intermediate in the production of pharmaceutically acceptable salts of clavulanic acid.

Particularly suitable pharmaceutically acceptable salts of clavulanic acid include alkali and alkaline earth metal salts, e.g. sodium, potassium, calcium or magnesium. The sodium and potassium salts are most suitable. The potassium salt is preferred.

The process according to the invention may be carried out for example as follows:

A solution of clavulanic acid in an organic solvent, preferably a ketone, an alcohol or an ester which is immiscible or only partly miscible with water, such as diethyl ketone, methyl isobutyl ketone, cyclohexanone, n-butanol, cyclohexanol, ethyl acetate, n-butyl acetate, preferably methyl isobutyl ketone or ethyl acetate, as produced by extraction of clavulanic acid from the fermentation broth or the filtrate thereof, is carefully freed from residual water, e.g. by azeotropic drying in vacuum or by adding a dehydrating agent such as magnesium sulphate. Then, 2-amino-2,4,4-trimethylpentane is added in pure form or as solution, whereby the corresponding amine salt of clavulanic acid separates as a crystalline solid. The process is effected at any non-extreme temperature, in general temperatures of from 0° to 35° C. are suitable, e.g. from 0° to 25° C. The precipitated salt is isolated by filtration and washed, and is further processed after drying or whilst moist with solvent.

If desired the 2-amino-2,4,4-trimethylpentane salt of clavulanic acid may be purified by recrystallisation. The recrystallisation may be carried out by dissolving the 2-amino-2,4,4-trimethylpentane salt of clavulanic acid in a suitable solvent or solvent mixture, which may be an alcohol, such as methanol, ethanol or isopropanol, or water or a mixture of water and a water-miscible organic solvent, such as isopropanol, tetrahydrofuran or acetone. The precipitation is effected by addition of a solvent, in which the 2-amino-2,4,4-trimethylpentane salt of clavulanic acid is only poorly soluble, such as e.g. tetrahydrofuran, acetone, diethyl ketone, methyl isobutyl ketone, methyl tert.butyl ether or n-butylacetate.

For the conversion of the 2-amino-2,4,4-trimethylpentane salt of clavulanic acid into a pharmaceutically acceptable salt of clavulanic acid, the intermediately-isolated amine salt is dissolved in an organic solvent, preferably an alcohol such as ethanol, isopropanol or butanol, whereby it is not necessary to add water in order to improve solubility. A solution of the desired alkali or alkaline earth metal salt as the salt of an organic carboxylic acid is added. Examples of suitable carboxylic acid salts are acetate, propionate or 2-ethylhexanoate. Preferably salts of 2-ethylhexanoic acid are used. This acid advantageously forms both readily-soluble alkali salts and 2-amino-2,4,4-trimethylpentane salts in the solvent used. The desired pharmaceutically acceptable salt of clavulanic acid, such as an alkali or alkaline earth metal salt, e.g. the potassium salt of clavulanic acid, thus precipitates in high yield and purity and is isolated by filtration, washing and drying.

The presently used 2-amino-2,4,4-trimethylpentane salt has considerable advantages over the amine salts of clavulanic acid used for the isolation and purification of clavulanic acid in EP-B-00 26 044 and EP-A-0 387 178. One essential advantage of the amine salt of clavulanic acid according to the invention is that it may be precipitated in crystalline form from the solution in a solvent suitable for extraction, without the addition of acetone. Thus recovery of the solvents employed, which has become increasingly important for ecological reasons, is considerably simplified. If one single solvent is used for extraction, the recovery of this solvent is simplified. Another advantage is the rapid crystallisation of the 2-amino-2,4,4-trimethylpentane salt of clavulanic acid in high yield and high purity, as well as the ready commercial availability of the base 2-amino-2,4,4-trimethylpentane.

A further advantage of the said salt is its excellent solubility in organic solvents employed for the conversion into pharmaceutically acceptable salts of clavulanic acid. The addition of water, which is necessary when using other amine salts of clavulanic acid, can thus be avoided.

The presently claimed process is suitable for industrial scale.

In the following examples, which illustrate the invention more fully without restricting it, all temperatures are given in degrees Centigrade.

EXAMPLE 1

100 ml of a dried methyl isobutyl ketone solution, which contains 30 g/l of clavulanic acid, is mixed whilst stirring with 2.5 ml of 2-amino-2,4,4-trimethylpentane. The mixture is stirred at room temperature for 30 minutes, cooled to 5° and stirred for 2 hours at this temperature. The precipitated deposit is filtered off, washed with methyl isobutyl ketone and is dried in vacuo at 30° to give 4.7 g (yield 95%) of crystalline 2-amino-2,4,4-trimethylpentane salt of clavulanic acid.

EXAMPLE 2

130 ml of a dried ethyl acetate solution, which contains 26 g/l of clavulanic acid, is mixed whilst stirring with a solution of 3.0 ml of 2-amino-2,4,4-trimethylpentane in 25 ml of ethyl acetate. The mixture is stirred at room temperature for 30 minutes, cooled to 15° and stirred for 3 hours at this temperature. The precipitated product is filtered off, washed with ethyl acetate and dried in vacuo at 30° to give 5,2 g (yield: 93%) of crystalline 2-amino-2,4,4-trimethylpentane salt of clavulanic acid.

EXAMPLE 3

To 4.0 l of a dried ethyl acetate solution of clavulanic acid, which has been obtained by extraction of a fermentation broth with ethyl acetate and concentrating the organic layer by vacuum distillation, are added 235 ml of 2-amino-2,4,4-trimethylpentane. The mixture is stirred at room temperature for 2 hours, cooled down to 5° and stirred over night at 5°. The precipitation is filtered off, washed with ethyl acetate and dried in vacuo at 30° to give 232 g of crystalline 2-amino-2,4,4-trimethylpentane salt of the clavulanic acid.

EXAMPLE 4

4.0 g of 2-amino-2,4,4-trimethylpentane salt of clavulanic acid from Example 1 or 2 are dissolved in 150 ml of isopropanol at 20° and 6.7 ml of a 2 M solution of potassium-2-ethylhexanoate in isopropanol are added. The mixture is stirred for 30 minutes at 20° and then cooled for 2 hours to 0–5°. The deposit is filtered off, washed with isopropanol and dried in vacuo at 30° to yield 2.7 g (yield 95%) of crystalline potassium clavulanate.

What is claimed is:

1. A process for the production of a pharmaceutically acceptable salt of clavulanic acid, which comprises forming the 2-amino-2,4,4-trimethylpentane salt of clavulanic acid and converting this salt into a pharmaceutically acceptable salt of clavulanic acid.

2. A process for the production of a pharmaceutically acceptable salt of clavulanic acid, which comprises the steps of:

a) treating a solution of clavulanic acid in an organic solvent with 2-amino-2,4,4-trimethylpentane;

b) isolating the 2-amino-2,4,4-trimethylpentane salt of clavulanic acid; and c) converting the obtained 2-amino-2,4,4-trimethylpentane salt of clavulanic acid into a pharmaceutically acceptable salt of clavulanic acid.

3. A process for the production of a pharmaceutically acceptable salt of clavulanic acid, comprising converting the 2-amino-2,4,4-trimethylpentane salt of clavulanic acid into a pharmaceutically acceptable salt of clavulanic acid.

4. A process of claim 1, wherein the pharmaceutically acceptable salt of clavulanic acid is an alkali or alkaline earth metal salt of clavulanic acid.

5. A process of claim 4, wherein the salt is an alkali salt.

6. A process of claim 4, wherein the salt is the potassium salt.

7. A process of claim 2, wherein the organic solvent is a ketone, an alcohol, or an ester which is immiscible or only partly miscible in water.

8. A process of claim 7, wherein the organic solvent is diethyl ketone, cyclohexanone, methyl isobutyl ketone, cyclohexanol, n-butanol, ethyl acetate, or n-butyl acetate.

9. A process of claim 2, wherein, in step a), the solution of clavulanic acid is obtained by extracting a fermentation broth, or a filtrate thereof, with an organic solvent.

10. A process of claim 9, wherein the organic solvent is diethyl ketone, cyclohexanone, methyl isobutyl ketone, cyclohexanol, n-butanol, ethyl acetate, or n-butyl acetate.

11. A process for the production of a pharmaceutically acceptable salt of clavulanic acid, which comprises the steps of:

a) treating a solution of clavulanic acid in an organic solvent with 2-amino-2,4,4-trimethylpentane;

b) isolating the 2-amino-2,4,4-trimethylpentane salt of clavulanic acid;

c) recrystallizing the product of step b); and d) converting the product of step c) into a pharmaceutically acceptable salt of clavulanic acid.

12. A process of claim 11, wherein the product of step b) is recrystallized by dissolving said product in alcohol, water, or a mixture of water and a water-miscible organic solvent.

13. A process of claim 12, wherein the alcohol is methanol, ethanol, or isopropanol.

14. A process of claim 12, wherein the water-miscible organic solvent is isopropanol, tetrahydrofuran, or acetone.

15. A process of claim 12, wherein recrystallization is effected by the addition of tetrahydrofuran, acetone, diethyl ketone, methyl isobutyl ketone, methyl t-butyl ether, or n-butyl acetate to said dissolved 2-amino-2,4,4-trimethylpentane salt of clavulanic acid.

16. A process of claim 2, wherein the product of step b) is a crystalline solid.

17. A method which comprises using the 2-amino-2,4,4-trimethylpentane salt of clavulanic acid as an intermediate in the production of a pharmaceutically acceptable salt of clavulanic acid.

18. A process of claim 2, wherein said converting is in a non-aqueous medium.

19. In a process of claim 2, the steps which comprise:

a) mixing a dried methyl isobutyl ketone solution which contains clavulanic acid with 2-amino-2,4,4-trimethylpentane;

b) stirring said mixture at room temperature for 30 minutes; and c) cooling said stirred mixture to 5° C. and stirring for 2 hours at 5° C. to isolate the crystalline 2-amino-2,4,4-trimethylpentane salt of clavulanic acid.

20. In a process of claim 2, the steps which comprise:

a) mixing a dried ethyl acetate solution which contains clavulanic acid with 2-amino-2,4,4- trimethylpentane in ethyl acetate;

b) stirring said mixture at room temperature for 30 minutes; and c) cooling said stirred mixture to 15° C. and stirring for 3 hours at 15° C. to isolate the crystalline 2-amino-2,4,4-trimethylpentane salt of clavulanic acid.

21. In a process of claim 2, the steps which comprise:

a) adding 2-amino-2,4,4-trimethylpentane to a dried ethyl acetate solution of clavulanic acid, which has been obtained by extraction of a fermentation broth with ethyl acetate and concentrating the organic layer by vacuum distillation;

b) stirring said mixture at room temperature for 2 hours; and c) cooling said stirred mixture to 5° C. and stirring overnight at 5° C. to isolate the crystalline 2-amino-2,4,4-trimethylpentane salt of clavulanic acid.

22. In a process of claim 2, the steps which comprise:

a) dissolving the 2-amino-2,4,4-trimethylpentane salt of clavulanic acid in isopropanol at 20° C.;

b) adding a solution of potassium-2-ethylhexanoate in isopropanol;

c) stirring said mixture for 30 minutes at 20° C.; and d) cooling said stirring mixture for 2 hours to 0–5° C. to produce crystalline potassium clavulanate.

* * * * *